United States Patent
Laermer

(10) Patent No.: US 11,986,823 B2
(45) Date of Patent: May 21, 2024

(54) MICROFLUIDIC DEVICE AND METHOD FOR THE NANOSTRUCTURE SEQUENCING OF NUCLEOTIDE STRANDS

(71) Applicant: Robert Bosch GmbH, Stuttgart (DE)

(72) Inventor: Franz Laermer, Weil der Stadt (DE)

(73) Assignee: Robert Bosch GmbH, Stuttgart (DE)

( * ) Notice: Subject to any disclaimer, the term of this patent is extended or adjusted under 35 U.S.C. 154(b) by 864 days.

(21) Appl. No.: 17/053,012

(22) PCT Filed: May 2, 2019

(86) PCT No.: PCT/EP2019/061247
§ 371 (c)(1),
(2) Date: Jan. 19, 2021

(87) PCT Pub. No.: WO2019/215005
PCT Pub. Date: Nov. 14, 2019

(65) Prior Publication Data
US 2021/0138465 A1 May 13, 2021

(30) Foreign Application Priority Data
May 8, 2018 (DE) ...................... 10 2018 207 098.9

(51) Int. Cl.
*B01L 1/00* (2006.01)
*B01L 3/00* (2006.01)
*C12Q 1/6806* (2018.01)
*C12Q 1/6869* (2018.01)

(52) U.S. Cl.
CPC ...... *B01L 3/502761* (2013.01); *C12Q 1/6806* (2013.01); *C12Q 1/6869* (2013.01); *B01L 2200/0663* (2013.01); *B01L 2300/0636* (2013.01); *B01L 2300/0896* (2013.01); *C12Q 2531/113* (2013.01); *G01N 2223/07* (2013.01)

(58) Field of Classification Search
None
See application file for complete search history.

(56) References Cited

U.S. PATENT DOCUMENTS

2014/0228255 A1* 8/2014 Hindson ............ C12N 15/1065
506/26
2016/0184829 A1 6/2016 Chiesl et al.

FOREIGN PATENT DOCUMENTS

WO 2014/024041 A1 2/2014
WO 2016/154337 A2 9/2016

OTHER PUBLICATIONS

Maier et al., "Neue Techniken zur Automatisierung in der DNA-Sequenzierung", Biocheme, Apr. 1, 1997 (11 pages).
(Continued)

*Primary Examiner* — Jyoti Nagpaul
(74) *Attorney, Agent, or Firm* — Maginot, Moore & Beck LLP

(57) ABSTRACT

A microfluidic device includes an array unit and a nanostructure connected to the array unit, wherein the array unit comprises array cells with substances for a polymerase chain reaction. The array cells include nucleotides with stop properties according to the Sanger sequencing method and primers for an asymmetric polymerase chain reaction. The nanostructure is configured to determine lengths of nucleotide strands formed by the polymerase chain reaction.

13 Claims, 2 Drawing Sheets

(56) References Cited

OTHER PUBLICATIONS

International Search Report corresponding to PCT Application No. PCT/EP2019/061247, dated Jul. 26, 2019 (German and English language document) (7 pages).

Hashimoto, M., et al.;On-line integration of PCR and cycle sequencing in capillaires; from human genomic DNA directly to called bases; Nucleic Acids Research, 2003, vol. 31, No. 8, 17 pages.

Blazej, Robert, et al.; Microfabricated bioprocessor for integrated nanoliter-scale Sanger DNA sequencing; Proceedings of the National Academy of Sciences, vol. 103, No. 19, May 9, 2006, pp. 7240-7245.

Bruijns, B., et al.; Microfluidic Devices for Forensic DNA Analysis: a Review; Biosensors, vol. 6, No. 41, Aug. 5, 2016, pp. 1-35.

* cited by examiner

MICROFLUIDIC DEVICE AND METHOD FOR THE NANOSTRUCTURE SEQUENCING OF NUCLEOTIDE STRANDS

This application is a 35 U.S.C. § 371 National Stage Application of PCT/EP2019/061247, filed on May 2, 2019, which claims the benefit of priority to Serial No. DE 10 2018 207 098.9, filed on May 8, 2018 in Germany, the disclosures of which are incorporated herein by reference in their entirety.

BACKGROUND

Several methods of DNA sequencing are known from the prior art for determining a nucleotide sequence in a DNA molecule, in particular the dideoxy method according to Sanger, also called chain termination synthesis, and referred to below as the Sanger sequencing method.

In this method, in four otherwise identical batches for a polymerase chain reaction (PCR), one of each of the four bases is added in part as dideoxynucleoside triphosphate (ddNTP) (i.e. one batch each of either ddATP, ddCTP, ddGTP or ddTTP). These chain termination ddNTPs have no 3'-hydroxyl group. If they are incorporated into the newly synthesised strand, it is no longer possible for the DNA to be extended by the DNA polymerase and DNA fragments of different lengths are produced, which always end with the same ddNTP in each individual batch (i.e. only with A or C or G or T per batch). These ddNTPs can be labeled with a radioactive probe, so that the lengths of these DNA fragments can be determined by gel electrophoresis and the nucleotide sequence can be determined by length comparison. Alternatively, sequencing can be performed by "time-of-flight" measurements by passing all PCR products through a channel restricted by a nanopore pair, as described for example in WO16154337A2.

Quantitative PCR (qPCR) is also known from the prior art, wherein the amplification of DNA fragments can be followed quantitatively in real time, in particular by means of fluorescence measurements.

SUMMARY

Against this background, the disclosure relates to a microfluidic device, in particular an array chip, combining a polymerase chain reaction (PCR) and a sequencing of nucleotide strands, in particular DNA fragments. The microfluidic device may in particular be an integratable part of a microfluidic environment, for example an array chip for integration into a lab-on-a-chip environment, for example in a microfluidic cartridge.

The microfluidic device comprises an array unit and a nanostructure connected to the array unit, wherein the array unit comprises array cells containing substances for carrying out a PCR. In particular, the array cells may be provided to carry out a quantitative PCR. The array cells contain nucleotides with stopping properties according to the Sanger sequencing method and primers for an asymmetric polymerase chain reaction. The nanostructure of the microfluidic device is configured to determine lengths of nucleotide strands formed by the polymerase chain reaction. Some or all primers may include a fluorescent label for optical monitoring of the PCR.

The nucleotide strands may in particular be DNA segments or DNA fragments obtained, for example, from sample preparation and sample purification, for example in combination with pre-amplification, particularly nested PCR or whole genome amplification (WGA). For example, the segments can be provided mixed with a PCR mix of polymerase, standard nucleotides (A, T, C, G) and required buffer salts in the array unit. In particular, the array unit may comprise a substrate in which the substrate has array cells in the form of recesses or depressions in which the PCR can take place. The substrate may be a substrate commonly used in microfluidics, especially composed of plastic.

An asymmetric polymerase chain reaction is understood in particular to be a PCR in which, in contrast to a classical PCR, the same number of amplified forward and reverse strands, particularly in terms of orders of magnitude, have not been produced at the end of the PCR. Asymmetric PCR, on the other hand, produces a different number of forward strands compared to reverse strands or vice versa, especially by orders of magnitude. In particular, asymmetric PCR has an exponential phase followed by a linear phase, in which in the exponential phase, forward strands and reverse strands are amplified fundamentally in equal numbers and in the linear phase only either forward strands or reverse strands are amplified.

Nucleotides having stop properties (stop nucleotides) according to the Sanger sequencing method are, in particular, dideoxyribonucleoside triphosphates (ddNTPs), so that one of the four ddNTPs for carrying out the Sanger sequencing method can be added to each PCR mixture in addition to the deoxyribonucleoside triphosphates (dNTPs).

A nanostructure can be understood to mean in particular a structure having structural elements in the nanometer size range. In particular, the nanostructure may have pores and/or channels with dimensions in the nanometer range, referred to below as nanopores or nanochannels.

The device according to the disclosure has the advantage that an automated sequencing of DNA segments can be integrated in a well-defined manner in a microfluidic environment, in particular in a lab-on-a-chip. The combination of the Sanger sequencing method using stop nucleotides with fragment length determination by the nanostructure makes it possible to dispense with the direct identification of nucleobases using nanopores or nanochannels. On the other hand, determination of the length of the PCR products is advantageously sufficient for the indirect determination of the base sequence, wherein it is possible to determine the length by means of a passage time through the nanostructure, which makes the determination particularly robust. By combining a PCR with a directly linked determination of the length of the PCR products via a nanostructure, the usual fluorescent labeling of the PCR products can also be advantageously dispensed with if necessary. If the array cells are provided to carry out a quantitative PCR (qPCR), the disclosed device allows the advantageous synergy of combining an asymmetric qPCR reaction with a directly linked nanostructure for the determination of the length of the PCR products generated. Monitoring of the qPCR reaction allows the exact determination of the transition from the exponential to the linear PCR phase and, after a series of linear amplification processes, it also allows an exact starting point of the passage process through the nanostructures with integrated length measurement of the products, by means of the passage times through the nanostructure.

In a particularly preferred configuration of the device, the primers in the array cells each comprise primer pairs with a majority primer type and a minority primer type, such that the asymmetric polymerase chain reaction has an exponential phase followed by a linear phase. The majority primer type differs from the minority primer type for example only in the relative number of primers, so that in relation to the number of primers the majority primer type dominates the minority primer type by preferably 1 to 3, very preferably 1 to 2 orders of magnitude. As long as a sufficiently large number of both primer types is present, asymmetry in their numbers has no effect, so that the PCR proceeds exponentially using both primer types. As soon as the minority primer is no longer available in sufficient numbers, the PCR enters the linear phase of amplification, i.e. increasingly only one strand, for example the forward strand, is transcribed and amplified. Preferably, one or more groups of array cells each comprise four array cells, with the array cells having the same types of primers for each of the groups. In other words, all array cells of each group have the same types of primers. For the purpose of optical monitoring of the PCR, the primers may have a fluorescent label. For example, either all primers or only certain primers can have such a label. For example, only primers of the majority primer type have such a label to also allow monitoring during the linear phase of the PCR. Alternatively, the primers of the majority primer type and the primers of the minority primer type may have different labels, which facilitates the observation of the transition from the exponential to the linear phase. Alternatively, only the primers of the minority primer type have a label.

The array cells thus preferably contain in each case a highly asymmetric number of majority and minority primers characteristic for the respective array cell or for the respective group of array cells, each specific for a characteristic DNA segment, combined with a stop nucleotide of type A*, T*, C* or G* according to the Sanger sequencing method characteristic for the respective array cell. During passage through the nanostructure connected to the array unit of sequence-specific DNA fragments, which end with the stop nucleotide characteristic for the respective array cell, generated mainly during the linear phase of the polymerase chain reaction, a change in electrical current flow can be measured according to an advantageous configuration and thus the passage time of the respective DNA fragment through the nanostructure can be determined. Thus, the respective length of the fragments passing through can be determined. The sum of all fragment lengths for each of four array cells with the same primers and stop nucleotides of type A*, T*, C* or G* (one type in each of the four array cells) gives the total DNA sequence of the corresponding DNA segment defined by the primers.

In a particularly advantageous further development, one or more suppressing primers, to prevent amplification of predetermined species during the polymerase chain reaction, are upstream in at least one array cell. Such suppressing primers, also known as "clamps", can be advantageously added to suppress amplification of certain species, for example non-mutated wild type DNA segments, when targeting detection of mutations differing from the wild type. The details of the deviations from the wild type advantageously need not be known, so that unknown mutations can also be decoded. It is also advantageous for wild type discrimination if the course of the PCR reaction is monitored as qPCR.

According to a particularly advantageous further development, individual array cells are assigned to individual detection structures of the nanostructure in such a way that one detection structure can determine lengths of nucleotide strands from one array cell in each case. Preferably one detection structure is in each case linked with one array cell. This has the advantage that PCR products detected by the detection structures can be clearly assigned to array cells. The detection structures may be, in particular, the aforementioned nanopores or nanochannels of the nanostructure or, for example, be channels that are restricted in each case by two nanopores.

In an advantageous configuration in this case, between individual array cells and individual detection structures, electrical voltages can be applied via electrodes to convey and determine the length of nucleotide strands.

The disclosure also relates to a method for sequencing nucleotide strands using the microfluidic device according to the disclosure. In a first step of the method, an asymmetric polymerase chain reaction is carried out with the array unit of the device to amplify the nucleotide strands according to the Sanger sequencing method. In a second step, the lengths of the amplified nucleotide strands are determined by the nanostructure of the device.

According to an advantageous further development of the method, the performance of the polymerase chain reaction is monitored. In this case, the monitoring preferably can be undertaken optically by means of a fluorescent label, for example by fluorescent labeling of one or more of the primers used. As described above, this advantageously allows monitoring of individual PCR cycles. In particular, the transition between exponential PCR and linear PCR can thus be detected and monitored. In addition, the number of linear PCR cycles can also thus be monitored in a simple manner in which preferably a predefined number of linear PCR cycles may be used as a criterion for starting the determination of fragment lengths by the nanostructures. In other words, the determination of fragment lengths is started after a predefined number of linear PCR cycles. This has the advantage that the amount of PCR products present at the end of the PCR may be adjusted in a simple manner for the subsequent length determination.

With regard to the advantages of the disclosed method, reference is also made to the aforementioned corresponding advantages of the device according to the disclosure and the further developments and configurations thereof.

BRIEF DESCRIPTION OF THE DRAWINGS

Working examples of the device and method are shown schematically in the figures and are further elucidated in the following description. The same reference numbers are used for the elements represented in the different figures and which have a similar effect, a repeated description of the elements thus being avoided.

Shown are

DETAILED DESCRIPTION

Figure 1:
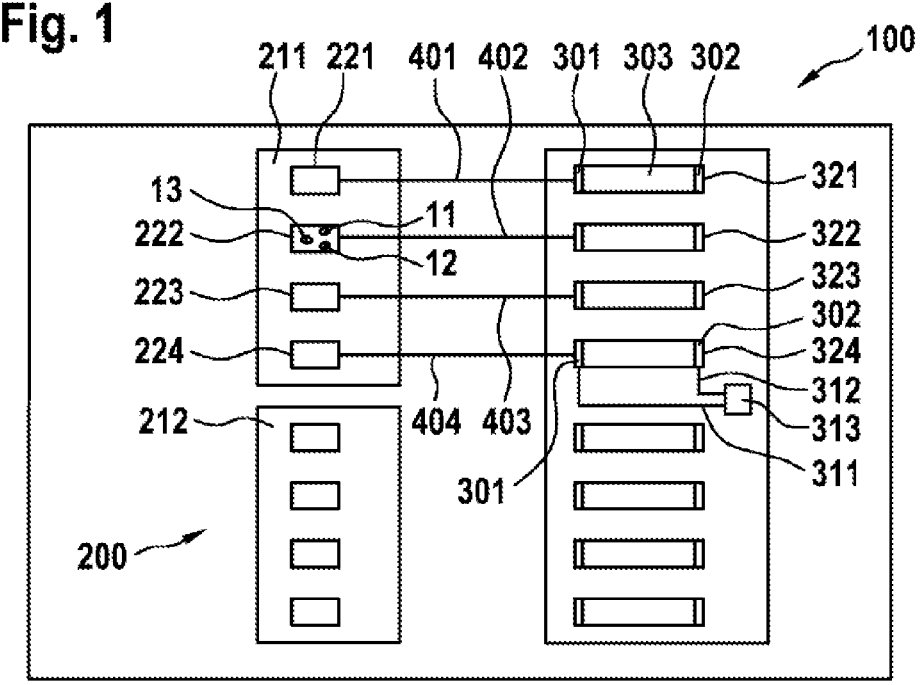
FIG. 1 A working example of the device according to the disclosure.

FIG. 1 shows schematically a working example of the microfluidic device 100 for sequencing nucleotide strands. The device 100 comprises an array unit 200 and a nanostructure 300 connected to the array unit 200.

The array unit 200 comprises one or more groups 211, 212 of array cells. FIG. 1 shows schematically a first group 211 and a second group 212 of array cells, wherein each group preferably comprises array cells 221, 222, 223, 224. In addition, however, the array unit may also comprise further groups of array cells. Substances 11, 12, are preferably pre-charged for carrying out a quantitative PCR (qPCR) in array cells 221, 222, 223, 224. In particular, the array cells each contain primer pairs 11, 12 with primers of a majority primer type 11 and a minority primer type 12. Further substances 13 comprise in particular selected nucleotides, for example freeze-dried substances for the PCR mixture.

In each case, four array cells 221, 222, 223, 224 of one group 211, 212 therefore each identically contain the same primer pair 11, 12 for the qPCR. In addition, these four array cells 221, 222, 223, 224 each contain a comparatively small number of one nucleotide type, for example in the lower percentage range, having stop properties, i.e. A*, T*, C* and G* according to the Sanger sequencing method. If, during a PCR cycle, such a nucleotide having stop properties is incorporated into the forward or reverse strand, the PCR is terminated and a corresponding PCR product fragment of a characteristic length is produced, which ends with the respective stop nucleotide. According to the Sanger sequencing method, after a sufficiently large number of PCR cycles, all DNA fragment lengths of forward and reverse strands are formed which end with the respective type of stop nucleotide presented.

As long as the PCR proceeds exponentially, determining the length of an amplified DNA fragment is uncharacteristic of the DNA sequence of the DNA fragment, because the PCR products of both the forward and reverse strand terminate at all sites matching the stop nucleotide. Preferably, the number of primers of the majority primer type 11 is therefore one to two orders of magnitude larger than the number of primers of the minority primer type 12. As long as a sufficient number of both primer types 11, 12 is available, the asymmetry in their numbers has no effect, so that the PCR proceeds exponentially with consumption of both primer types and a large number of PCR products are formed in a short time.

As soon as the minority primer 12 is no longer available in sufficient numbers, the PCR enters the linear phase of amplification, i.e. increasingly only the strand amplified by the majority primer is amplified, for example the forward strand (in the following, only the forward strand is considered, without any restriction of the generality). The incorporation of stop nucleotides increasingly results in DNA fragment lengths that are characteristic of the sequence of the forward strand. During the exponential phase of the PCR, an uncharacteristic "background" of fragment lengths is formed, whereas during the linear phase of the PCR characteristic fragments are formed which reflect information about the sequence. Since the PCR as qPCR can be quantitatively controlled during its course, the transition to the linear phase and to the "characteristic PCR cycles" can be clearly recognized, so that the entire process can be controlled in a well-defined manner. In particular, the qPCR can be effectively monitored as described above using fluorescent labeling, for example of the primers.

The nanostructure 300 connected to the array cells 210, 211, 211, 221, 222, 223, 224 is configured to determine the lengths of DNA fragments amplified by PCR. FIG. 1 shows schematically that preferably individual detection structures 321, 322, 323, 324 of the nanostructure 300 are assigned to the individual array cells 221, 222, 223, 224 in such a way that each detection structure 321, 322, 323, 324 can determine lengths of nucleotide strands each from one array cell 221, 222, 223, 224. In other words, each array cell 221, 222, 223, 224 is connected to its own detection structure 321, 322, 323, 324, for example via microfluidic channels 401, 402, 403, 404. The detection structures 321, 322, 323, 324 can in particular be nanopores or nanochannels, for example channels 303, which are each restricted by two nanopores as inlet and outlet 301, 302.

Figure 2:
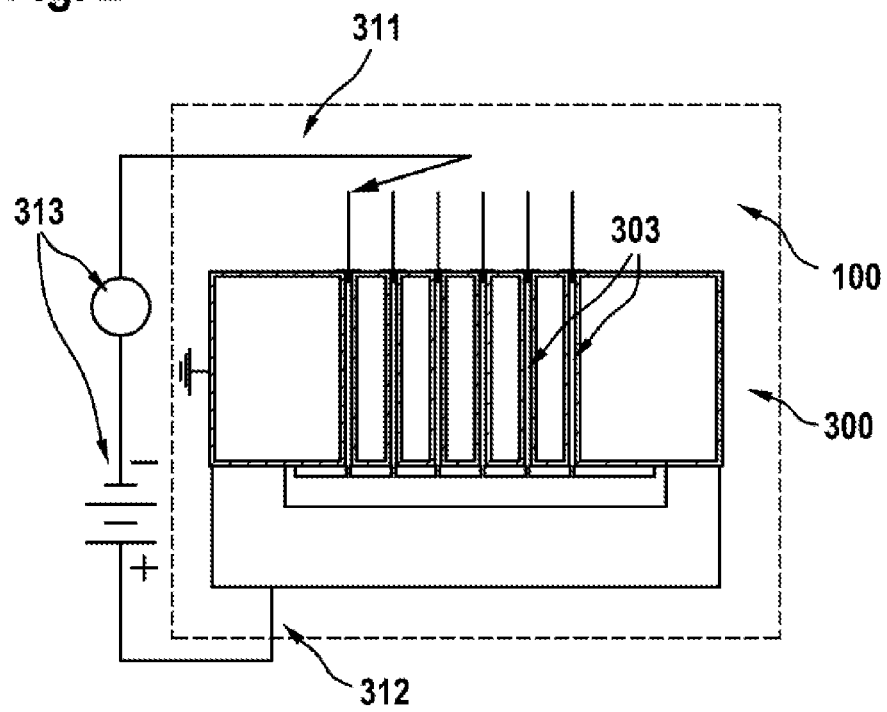
FIG. 2 another working example of the device according to the disclosure.

The detection structures 321, 322, 323, 324 are preferably equipped with electrode geometries 311, 312, 313 to detect the passage of a DNA fragment through a detection structure 321, 322, 323, 324 by means of a change of current or voltage. For example, the current flow in each case is interrupted or changed as long as a DNA fragment passes through the detection structure 321, 322, 323, 324, i.e. for example, passes through the nanopore or the nanochannel 303 and passes the electrode geometry. A length of the DNA fragment can be determined by measuring the passage times through the respective detection structure 321, 322, 323, 324. Since each measured length uniquely identifies the position of the corresponding stop nucleotide, the sum of all measured lengths from an array cell 221, 222, 223, 224 gives the total of all stop nucleotide positions and information from the four array cells 221, 222, 223, 224, a group 211, 212 together give the respective total gene sequence for all four stop nucleotide types. All array cells together thus yield the sequences of all DNA fragments to be analyzed. The maximum length of the fragments occurring per array cell (i.e. the length of the full DNA strand) and the minimum length of the fragments occurring per array cell (i.e. the length of the forward primer in this example) also enables an in-situ calibration of the length scale. Furthermore, the electrode geometry 311, 312, 313 can also be used to convey the DNA fragments, which are usually electrically charged. FIG. 2 shows a possible configuration of the nanostructure 300 with nanochannels 303 arranged in parallel, which can be subjected to a voltage by means of electrodes 311, 312 and a voltage source 313.

As a simplified illustration, it is assumed that after N cycles of exponential amplification by a factor of 2 per PCR cycle, the qPCR in an array cell transitions abruptly to a linear phase with subsequent M linear amplification steps (in reality this transition is of course "smeared", but this does not fundamentally change anything in terms of understanding and qualitative estimation).

After N exponential and M linear PCR cycles, the relative fraction R of the characteristic (the "correct") terminated fragments is:

$$R = \frac{2^N - 1 + 2^N M}{2(2^N - 1) + 2^N M} = \frac{1 + \frac{2^N M}{2^N - 1}}{2 + \frac{2^N M}{2^N - 1}} = \frac{1 + \frac{M}{1 - 2^{-N}}}{2 + \frac{M}{1 - 2^{-N}}} \approx \frac{1 + M}{2 + M} \xrightarrow{for\ M \to \infty} 1$$

Correspondingly, the fraction F of the non-characteristic (the "wrong") terminated fragments is:

$$F = \frac{2^N - 1}{2(2^N - 1) + 2^N M} = \frac{1}{2 + \frac{2^N M}{2^N - 1}} = \frac{1}{2 + \frac{M}{1 - 2^{-N}}} \approx \frac{1}{2 + M} \xrightarrow{for\ M \to \infty} 0$$

It is apparent from this that a good signal-to-noise ratio can be achieved with an appropriate number of linear PCR cycles of e.g. 10-20, i.e. the "correct" fragment lengths appear accordingly in the count statistics with a 10-20 fold higher count rate than the "wrong" fragment lengths.

Figure 3:
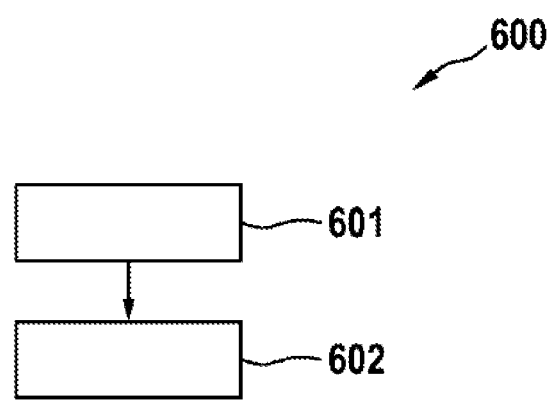
FIG. 3 a flow diagram of a working example of the method according to the disclosure.

FIG. 3 shows a flow diagram of a working example of the method 600 according to the disclosure for sequencing nucleotide strands which may be carried out, for example, using a working example of the device 100 in accordance with FIGS. 1 and 2. In a first step 601 of the method 600, the asymmetric polymerase chain reaction is carried out using the array unit 200 of the device 100 for amplification of nucleotide strands according to the Sanger sequencing method. In a second step 602, the lengths of the amplified nucleotide strands are determined by the nanostructure 300 of the device 100. Preferably, the determination of the lengths can be started as described above after a given number of PCR cycles have been carried out, especially after a given number of cycles of linear PCR. The PCR and especially the PCR cycles can be monitored here as detailed above using fluorescent labeling.

The invention claimed is:

1. A microfluidic device for sequencing nucleotide strands, the microfluidic device comprising:
    an array unit comprising array cells having substances for an asymmetric polymerase chain reaction, the array cells including nucleotides having stop properties according to the Sanger sequencing method and primers for the asymmetric polymerase chain reaction; and
    a nanostructure connected to the array unit and configured to determine lengths of nucleotide strands formed by the polymerase chain reaction.

2. The microfluidic device as claimed in claim 1, wherein the primers in each array cell include primer pairs with a majority primer type and a minority primer type, such that the asymmetric polymerase chain reaction has an exponential phase followed by a linear phase.

3. The microfluidic device as claimed in claim 1, wherein the nanostructure comprises nanopores and/or nanochannels.

4. The microfluidic device as claimed in claim 1, wherein:
    one or more groups (211, 212) of the array cells each comprise four array cells, and
    all array cells of a group of the one or more groups of array cells have the same types of primers.

5. The microfluidic device as claimed in claim 1, wherein each individual array cell of the array cells is assigned to a detection structure of the nanostructure in such a way that each detection structure determines the lengths of nucleotide strands from one array cell.

6. The microfluidic device as claimed in claim 5, further comprising:
    electrodes configured to apply an electrical voltage between the individual array cells and the corresponding detection structures to convey and determine the length of nucleotide strands.

7. The microfluidic device as claimed in claim 1, wherein at least one array cell includes one or more suppressing primers located upstream for preventing amplification of predefined species during the asymmetric polymerase chain reaction.

8. A method for sequencing nucleotide strands using a microfluidic device, comprising:
    performing an asymmetric polymerase chain reaction with an array unit (200) of the device to amplify the nucleotide strands by the Sanger sequencing method; and
    determining lengths of the amplified nucleotide strands with a nanostructure of the device.

9. The method as claimed in claim 8, wherein the asymmetric polymerase chain reaction has an exponential phase followed by a linear phase.

10. The method as claimed in claim 9, further comprising: monitoring the asymmetric polymerase chain reaction.

11. The method (600) as claimed in claim 10, further comprising:
    detecting or monitoring a transition between the exponential phase and the linear phase; and/or
    monitoring the number of linear phase cycles using the monitored number as a criterion for starting the determination of the lengths with the nanostructures.

12. The method as claimed in claim 10, wherein the monitoring of the asymmetric polymerase chain reaction includes monitoring the asymmetric polymerase chain reaction via fluorescent labeling of one or more primers.

13. The method as claimed in claim 9, wherein the exponential phase includes a quantitative polymerase chain reaction.

* * * * *